United States Patent

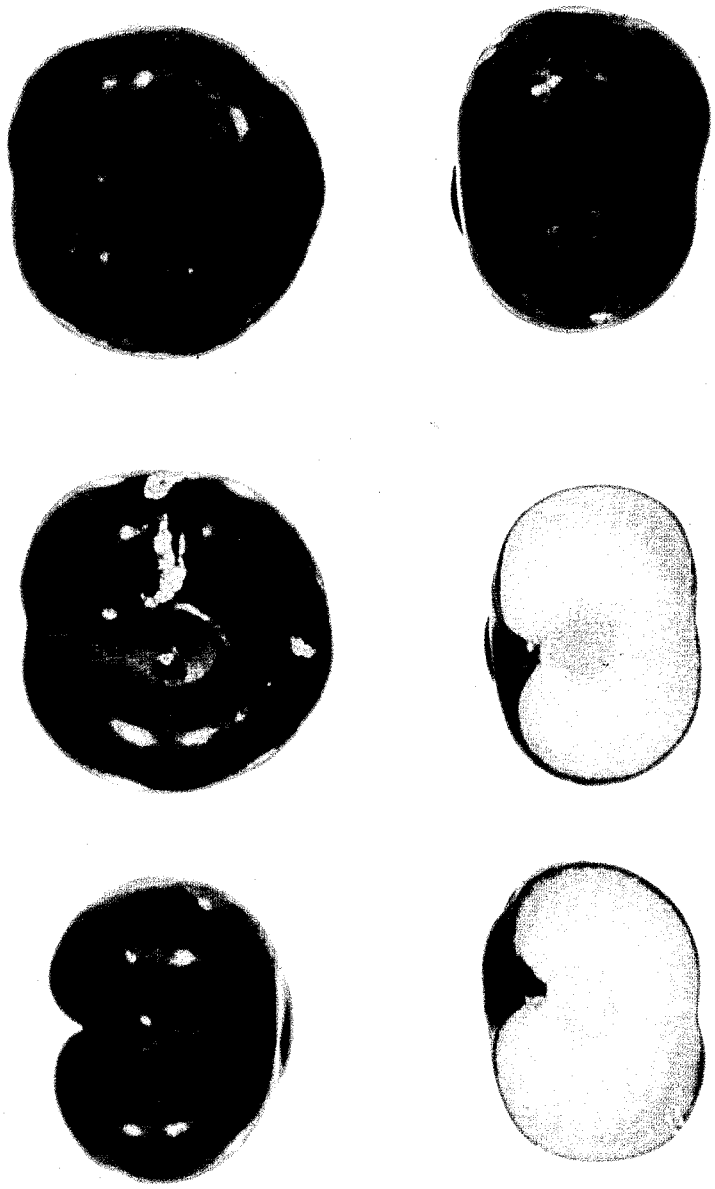

Plant Pat. 3,925

Patented June 22, 1976

3,925

PLUM TREE

Claron O. Hesse, Kingsburg, Calif., assignor to The Regents of the University of California, Berkeley, Calif.

Filed July 7, 1975, Ser. No. 593,391

Int. Cl. A01h *5/03*

U.S. Cl. Plt.—38 1 Claim

This invention relates to a new and distinct variety of plum tree which resulted from a cross, the pedigree of which is set forth below:

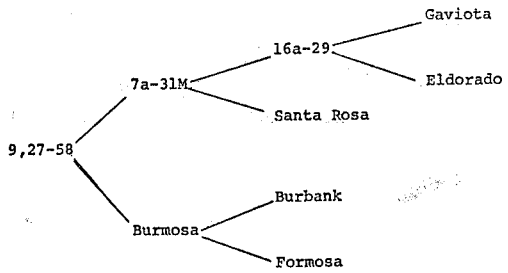

The invention of Selection 9, 27–58 was discovered in 1969 and subsequently asexually multiplied at the Kearney Horticultural Field Station, Fresno County, Calif., in 1970. Thereafter the new variety was placed in several authorized grower-cooperative trial plots and tested. These tests indicated the merit of this new plum tree and resulted in its selection as a promising variety.

FIG. 1 of the accompanying drawing illustrates plums of the new variety which are typical in size, shape and color, some of which are shown in half sections, pitted, and in which some of the variations in the size and shape of the fruit, and the color of the skin and flesh of this variety are indicated.

One of the outstanding chartacteristics which distinguish the variety from others is the early maturity of its fruit. Shipping maturity is from two to three days earlier than Red Beaut (Plant Pat. 2,539) to one to two days later than Red Beaut, depending upon the season. It differs from Red Beaut by being flatter in shape, darker in external coloration, and of higher edible quality. The fruit is of excellent eating quality in that its flavor is rich, distinctive, sweet, mildly subacid and highly aromatic.

The varietal characteristics of this new plum tree described below in detail were observed upon its discovery and subsequently through its test period. The color terminology as used herein is in accordance with Ridgway, Color Standards and Color Nomenclature (1912 edition).

TREE

*Size*—Vigorous, upright-spreading.

*Young Shoot*—Bark, green (Lettuce Green, Plate V), becoming brown (Argus Brown, Plate III) with age.

*Scaffold Bark*—Brown (Carob Brown, Plate XIV), rough, longitudinally striated showing light brown beneath (Pale, Ochraceous-Salmon, Plate XV).

*Foliage Buds*—Small, brown to reddish brown (Chestnut Brown, Plate XIV to Carob Brown, Plate XIV), glabrous.

*Flower Buds*—Small, brown to reddish brown (Prout's Brown, Plate XV to Mahogany Red, Plate II), glabrous; 2 or more per node.

*Spurs*—Short, 1–10 cm., numerous, floriferous.

FLOWERS

*Number*—Two to three per bud, abundant, about 2.5 cm. across when fully open.

*Pedicel*—Medium length, 7.4±0.55 mm., medium thick. Scheele's Green, Plate VI.

*Corolla*—Rather short, obconic; glabrous; slightly rugose, pebbled; Scheele's Green, Plate VI. Nectaries bright orange (Orange, Plate I) when young to slightly dark greenish yellow (Dull Green Yellow, Plate XVII) when open; irregularly grooved longitudinally to point of stamen insertion.

*Calyx*—Lobes separate; oval, about 4 mm. long x 2 mm. wide at base; apex blunt, nearly rounded; sparsely and irregularly denticulate laterally and toward apex; color Parrot Green, Plate VI, becoming dull light yellow (Chalcedony Yellow, Plate XVII) with age; slightly rosaceous (Pompeian Red, Plate XIII) near margin, denticles light, bright red (Tyrian Red, Plate XII). Lobes reflexed ca. 75–95° at anthesis, cupped or nearly keeled. Inner surface greenish white (Pale Lumiere Green, Plate XVII), glistening.

*Petals*—White, broad oval, 11.5±1.00 mm. long x 8.4±0.82 mm. wide, more or less cupped, apex rounded; base broadly acuminate to a short, rather broad claw. Margin somewhat wavy. Petals upright-spreading when fully open.

*Stamens*—Filaments white, slender, variable in length, longest 28.2±1.48 mm. and about equal to the pistil insertion. Anthers plump; brownish amber (Light Cadmium, Plate IV), lightly tinged red (Nopal Red, Plate I), especially apically. Pollen moderately abundant, yellow (Lemon Chrome, Plate IV), fertile.

*Pistil*—Ovary oval, green (Parrot Green, Plate VI). Style long, 9 to 11 mm., whitish, medium thickness with scattered white hairs of medium length on basal ½. Stigma blunt, capitate, small.

LEAVES

Midshoot leaves from moderately vigorous shoots.

*Shape*—Oval to slightly obovate, 10.5±0.77 cm. long (with petiole) x 4.42±0.25 cm. wide; base acuminate, apex acuminate.

*Petiole*—Short, length 1.1±0.12 cm., stout, channeled on ventral side with 6–10 glands; the upper pair may be on leaf blade. Glands Parrot Green, Plate VI. Petiole color, greenish (Parrot Green, Plate VI), with red tinge (Pansy Purple, Plate XII) where exposed. Nearly glabrous dorsally; more or less puberulent ventrally along and in the petiole channel.

*Leaf Blade*—Thin, green ventrally (Cedar Green, Plate VI); lighter greyish green dorsally (Deep, Dull Yellow-Green, Plate XXXII). Midrib puberulent, especially basally and in main lateral vein axils; otherwise glabrous.

*Margin*—Finely crenate; usually doubly or triply; crenations tipped with a small brown (Chestnut, Plate II) gland; basal and apical crenations often single and sometimes without the gland. Margins somewhat wavy; blade flat or nearly so.

*Spur Leaves*—Size; basal leaves small becoming larger toward spur apex. Typical apical leaves about 8.40±0.34 cm. long (with petiole) x 2.92±0.19 cm. wide. Petiole 1.38±0.11 cm.

*Shape*—Ovovate; base rather acute acuminate; apex acuminate. Margin crenate, crenations usually single with or without glands. Petioles slenderer than those of shoot leaves; usually with 2 glands (±1) on the petiole or one on a basal leaf crenation. Petiole and midrib less pubescent than for shoot leaves. Color same.

FRUIT

*Size*—Medium. 44.7±2.0 mm. axial length x 56.98±2.2 mm. cheek diameter x 54.9±2.4 mm. suture diameter. Fruit weight 82.7±10.5 gms.

*Ripe*—In 1973, ripe on May 27. In 1973, shipping ripe on May 23.

*Crop*—Very light.

*Shape*—Cheek and suture aspect: oblate. Axial aspect: nearly round, flattened on suture side.

*Shoulders*—Very broad, rounded to nearly flat; smooth, higher laterally; broadly and shallowly depressed dorsally; rather broadly grooved to occasionally creased ventrally.

*Cavity*—Moderately deep conic; oval in outline.

*Stem*—Short to medium, thick, woody; color greenish brown to brown (Light Bice Green, Plate XVII to Citrine, Plate IV).

*Suture*—A broad, shallow groove from base to apex, becoming shallower apically. Lips usually broad, flat to rounded.

*Apex*—Pistil scar a small dot, usually obscure; depressed; with a more or less pronounced bulge dorsally and slightly less so ventrally to nearly flat on smaller specimens. Generally broad to flat.

*Color*—Red (Bordeaux, Plate XII) to dark red (Blackish Red-Purple, Plate XII) at full maturity. Full colored.

*Bloom*—Medium, light grey (Deep Plumbeous, Plate LII).

*Dots*—Very obscure; tiny, light brown (Light Pinkish Cinnamon, Plate XXIX); only moderately numerous; on sides laterally and dorsally.

*Flesh*—Color; greenish-amber (Pyrite Yellow, Plate IV) to Old Gold, Plate XVI, becoming darker near the skin. Usually with a narrow red streak from stone apex to fruit apex.

*Texture*—Firm, meaty, juicy.

*Skin*—Medium thick; moderately tough.

*Cavity*—Slightly darker than flesh color (Isabella Color, Plate XXX).

*Flavor*—Fruit aroma high; flavor rich, distinctive, sweet, mildly subacid, excellent.

STONE

*Adhesion*—A tight freestone; size less than medium; 16.96±1.15 mm. long x 9.7±0.45 mm. cheek diameter x 18.28±1.36 mm. suture diameter.

*Shape*—Broad oval to slightly broad obovate; variable; irregular in outline. Narrow obovate in suture veins.

*Base*—Rounded or slightly depressed. Narrow. Obscure; sometimes more or less necked.

*Cheeks*—Slightly rugose.

*Dorsal Edge*—Narrow, keeled, somewhat protruding; wings rather narrow, barely raised; groove very shallow.

*Apex*—Flat with a short, blunt tip.

*Color*—Tan, light (Ochraceous Buff, Plate XV).

*Seed*—Medium size, ovate, more or less asymmetrical. At maturity seed coats light (whitish) colored.

I claim:

1. The new and distinct variety of plum tree herein described and illustrated, and identified by the characteristics enumerated above.

No references cited.

ROBERT E. BAGWILL, Primary Examiner